US00PP31806P2

(12) United States Plant Patent
Van Swieten

(10) Patent No.: US PP31,806 P2
(45) Date of Patent: May 26, 2020

(54) ***PHALAENOPSIS* ORCHID PLANT NAMED 'PHALGRYCHI'**

(50) Latin Name: ***Phalaenopsis* hybrid**
Varietal Denomination: PHALGRYCHI

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,657

(22) Filed: May 17, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGRYCHI', particularly characterized by having white and flecked flowers with greenish-yellow and white lips, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGRYCHI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGRYCHI'.

The new *Phalaenopsis* plant is a product of a planned breeding program conducted by the inventor in Bleiswijk, the Netherlands. The objective of this breeding program was to create a new *Phalaenopsis* plant with numerous attractive white and flecked flowers with greenish-yellow and white lips, suitable for potted plant production.

The new *Phalaenopsis* plant 'PHALGRYCHI' is a result of cross-pollination made by the inventor in February 2010 in Bleiswijk, the Netherlands, of the proprietary female, or seed parent, *Phalaenopsis* hybrid '01-2167' (unpatented) with the proprietary male, or pollen parent, *Phalaenopsis* hybrid '22444-010' (unpatented).

The new *Phalaenopsis* was selected by the inventor as a single plant within the progeny of the stated cross-pollination in a controlled greenhouse in Bleiswijk, the Netherlands, in October 2012. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Plant Breeder's Rights for this variety have been applied for in the European Union on Apr. 26, 2018, by Applicant who obtained the subject matter disclosed directly from the Inventor. 'PHALGRYCHI' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, the Netherlands, and can be used to distinguish 'PHALGRYCHI' as a new and distinct variety of *Phalaenopsis* plant:

1) White and flecked flowers with greenish-yellow and white lips (the intensity and number of flecks depends on the temperature during the growing period);
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in March 2019. Colors in the photographs may differ from the color values cited in the detailed botanical description, which accurately describe the actual colors of the new variety.

DESCRIPTION OF THE NEW VARIETY

Figure 1:
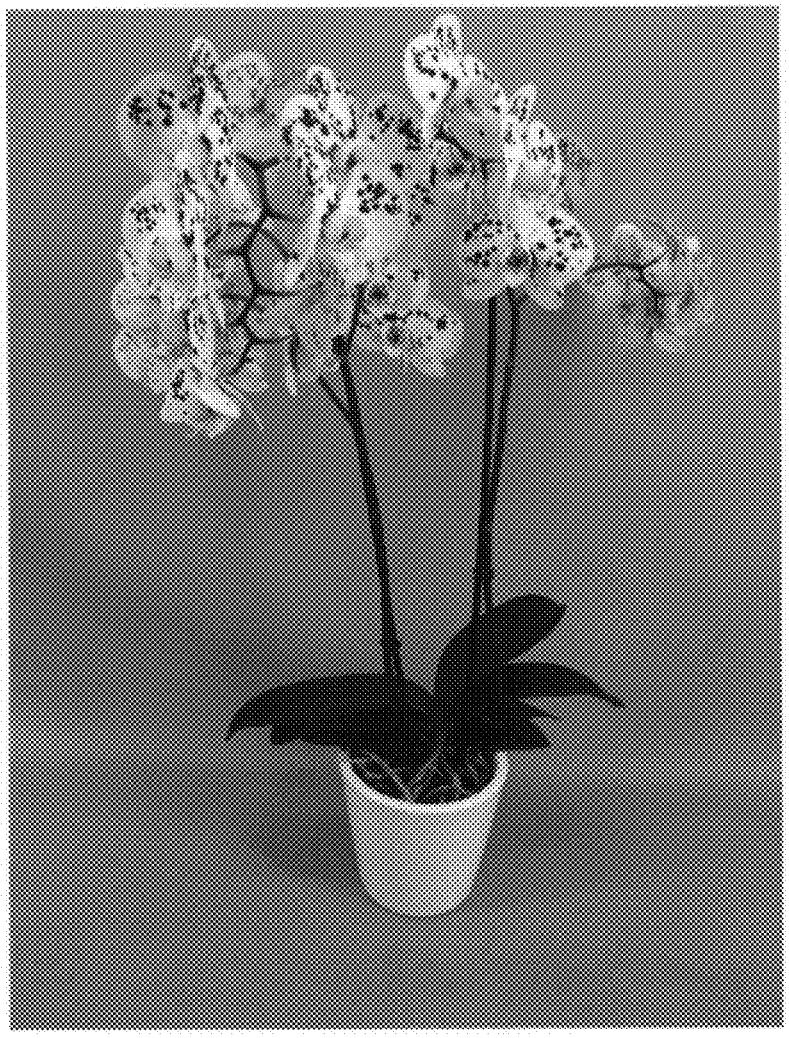
FIG. 1 shows the overall plant habit, including blooms and foliage of 'PHALGRYCHI'.
Figure 2:
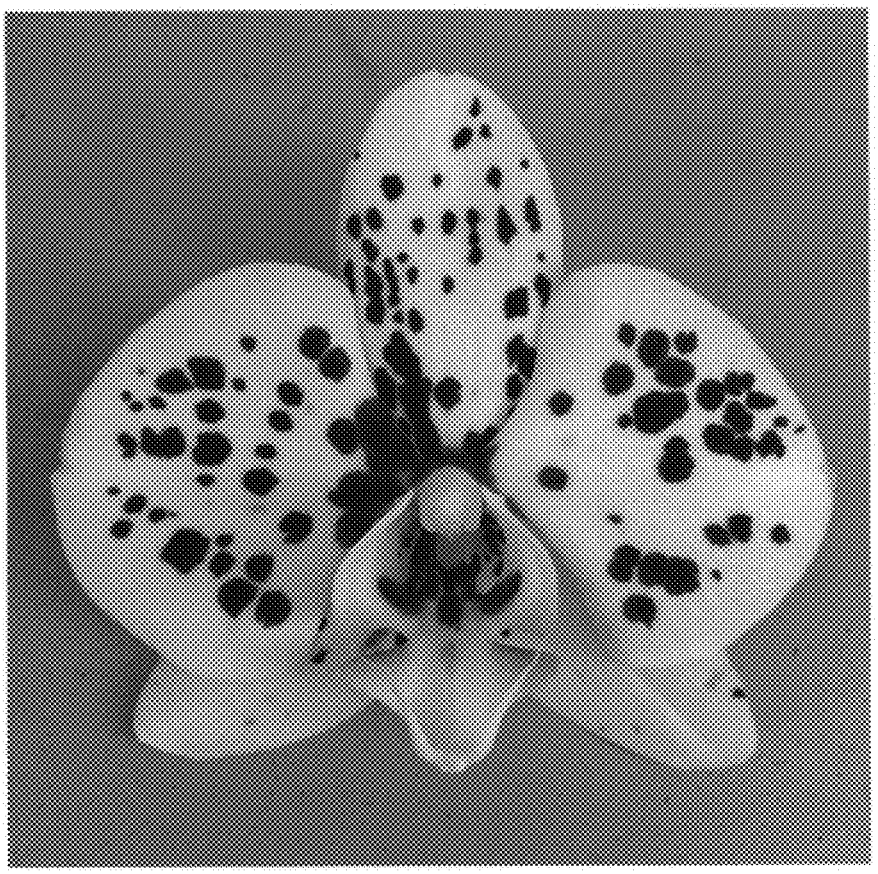
FIG. 2 shows a close-up of a flower of 'PHALGRYCHI'.
Figure 3:
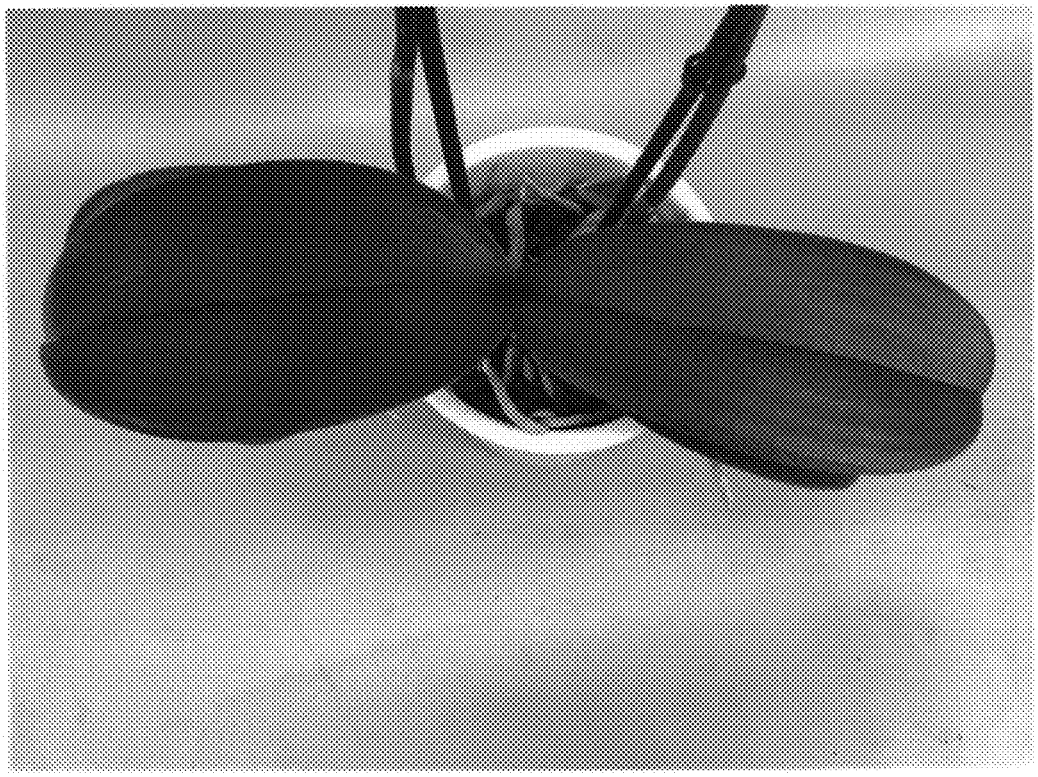
FIG. 3 shows an overhead view of the leaves of 'PHALGRYCHI'.

The following detailed description sets forth the distinctive characteristics of 'PHALGRYCHI'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in March 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGRYCHI'.

Parentage:

*Female parent*.—*Phalaenopsis* cultivar '01-2167' (unpatented).

*Male parent*.—*Phalaenopsis* cultivar '22444-010' (unpatented).

Propagation:

*Type*.—Meristem tissue culture.

Roots:

*Root description*.—Greyed-green (between RHS 190B and 190C) colored roots with branching lateral roots having light yellow-green (RHS 145B) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with panicle inflorescence.

*Height* (*from soil level to top of inflorescence*).—Approximately 64.0 cm to 69.0 cm.

*Width* (*measured from leaf tips*).—About 35.0 cm to 37.0 cm.

*Vigor*.—Moderate.

Leaves:

*Mature leaves*.—Quantity per plant: 7 to 9 leaves are produced before flowering. Length (fully expanded): 17.0 cm to 20.0 cm. Width: 8.0 cm to 9.0 cm. Shape: Oblong. Base shape: Moderately elongated. Apex: Obtuse unequal. Leaf blade angle with the petiole (measured from the horizontal position): Between 15 degrees and 25 degrees. Leaf margin: Entire. Color: Upper surface: RHS 147A. Lower surface: RHS 146B. Texture (both upper and lower surfaces): Rough. Thickness: 2.0 mm to 3.0 mm. Venation: Pattern: Parallel. Color of the midvein: Upper surface: RHS 147A. Lower surface: RHS 146A.

Peduncle:

*Quantity per plant*.—1 to 3.

*Number of flowers per peduncle*.—14 to 24.

*Length*.—64.0 cm to 69.0 cm.

*Diameter*.—6.0 mm to 7.0 mm.

*Strength*.—Strong.

*Aspect*.—Upright to slightly pendant.

*Texture*.—Smooth.

*Color*.—Green (mix of RHS 146B and 146C) with a touch of brown (RHS N200A).

*Internode length*.—4.0 cm to 6.0 cm.

Inflorescence description:

*Appearance*.—Upright to slightly pendant, panicle inflorescence with bilaterally symmetrical flowers that open in succession beginning with the lowermost flower.

*Number of inflorescences*.—1 to 3.

*Inflorescence size*.—Height (from base to tip): 260.0 mm to 340.0 mm.

*Flowering time*.—First flowers can be expected 10 to 11 months after planting in a 12-cm pot.

*Flower*.—Height: 87.0 mm to 92.0 mm. Diameter: 95.0 mm to 100.0 mm. Depth of lip: 29.0 mm to 31.0 mm.

*Flower longevity*.—On the plant: 16 to 24 weeks.

*Fragrance*.—Absent.

*Flower bud*.—Average size: Large. Length: 20.0 mm to 22.0 mm. Width: 20.0 mm to 22.0 mm. Shape: Round asymmetric (broad at the base and smaller toward tip). Color: Yellow-green (RHS 144C), flecked (RHS N77A) with a touch of light purplish-red (RHS NN74C).

*Petals*.—Arrangement: Open/free. Shape: Semi-circular. Apex: Slightly emarginated asymmetric. Margin: Slightly wavy. Length (from base to tip): 43.0 mm to 45.0 mm. Width: 52.0 mm to 54.0 mm. Position of the broadest part of the petal: At the base. Color (when fully opened): Upper surface: Basic color: White (RHS NN155C). Over color: Dark purplish-red flecks (RHS N79C; the intensity and number of flecks depends on the temperature during the growing period). Lower surface: Basic color: White (RHS NN155C). Over color: Diluting red-purple dots (from RHS N79C to N79D).

*Dorsal sepal*.—Shape: Elliptic. Apex: Emarginated symmetric. Margin: Entire. Length (from base to tip): 48.0 mm to 50.0 mm. Width: 32.0 mm to 34.0 mm. Color (when fully opened): Upper surface: Basic color: White (RHS NN155C). Over color: Dark purplish-red flecks (RHS N79B and RHS N79C). Lower surface: Basic color: White (RHS NN155C). Over color: Very light purple shade (RHS 76C); diluting dots (from RHS N79C to N79D).

*Lateral sepals*.—Shape: Ovate. Apex: Obtuse asymmetric. Margin: Entire. Length (from base to tip): 50.0 mm to 52.0 mm. Width: 28.0 mm to 30.0 mm. Color (when fully opened): Upper surface: Basic color: White (RHS NN155C). Over color: Light yellow-green (RHS 145D) at base and dark red-purple flecks (RHS N79C). Lower surface: Basic color: White (RHS NN155C). Over color: Light yellow-green (RHS 145C) at base and diluting red-purple flecks (from RHS N79C to N79D).

*Labellum* (*lip*).—Whiskers: Present. Length of whiskers: 21.0 mm to 23.0 mm. Color of whiskers: White (RHS NN155C) with few flecks (RHS N79C) and light greenish-yellow tips (RHS 1C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 21.0 mm to 23.0 mm. Width: 16.0 mm to 18.0 mm. Color: Dark red stripe (RHS 187C) at the base; white (RHS NN155C); greenish-yellow (RHS 3A) on one side.

*Apical lobe*.—Shape: Triangular (broad at the base). Margin: Entire. Length: 20.0 mm to 22.0 mm. Width: 26.0 mm to 28.0 mm. Color: Greenish-yellow wings and at the base (RHS 151C) with a touch of brown (RHS 175B); white towards whiskers (RHS NN155C).

*Callus*.—Average size: Medium to large. Height: 7.0 mm to 8.0 mm. Length: 6.0 mm to 7.0 mm. Width: 4.0 mm to 5.0 mm. Color: Dark red (between RHS 187A and 187B) with a touch of yellow (RHS 7B).

Reproductive organs:

*Column*.—Length: 9.0 mm to 11.0 mm. Diameter: 5.7 mm to 6.0 mm. Color: White (RHS NN155C).

*Pollinia*.—Quantity: 2. Diameter: 0.9 mm to 1.1 mm. Color: Orange (RHS 24A).

*Ovary*.—Length: 12.0 mm to 14.0 mm. Diameter: 2.2 mm to 2.4 mm. Color: Light yellow-green (RHS 145D) with a touch of very light purple (RHS 76C) toward the flower.

*Pedicel*.—Length: 43.0 mm to 45.0 mm. Diameter: 2.6 mm to 2.8 mm. Color: Dark purplish-red (RHS N79B) at the base; light yellow-green (RHS 145B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGRYCHI' differs from female parent plant '01-2167' (unpatented) in that 'PHALGRYCHI' has a flecked flower pattern, white columns, and emarginated dorsal sepal apexes, whereas '01-2167' has a flecked flower pattern that is shaded at the apex, purplish-pink columns, and obtuse dorsal sepal apexes. Additionally, 'PHALGRYCHI' has smaller flowers than '01-2167'.

'PHALGRYCHI' differs from male parent plant '22444-010' (unpatented) in that 'PHALGRYCHI' has a flecked flower pattern and calluses that are dark red with a touch of yellow, whereas '22444-010' has an even flower pattern and calluses that are yellow and dotted (RHS 172A). Additionally, 'PHALGRYCHI' has larger flowers than '22444-010'.

'PHALGRYCHI' is most similar to the commercial *Phalaenopsis* plants named 'PHALYDSAP' (U.S. Plant Pat. No. 29,388) and 'PHALIFSIB' (U.S. Plant Pat. No. 27,459). 'PHALGRYCHI' differs from the commercial variety 'PHALYDSAP' in that 'PHALGRYCHI' has whiskers that are white with few flecks of RHS N79C and light greenish-yellow tips, whereas 'PHALYDSAP' has whiskers that are reddish-purple with white tips. Additionally, 'PHALGRYCHI' has longer whiskers and larger flowers than 'PHALYDSAP'.

'PHALGRYCHI' differs from the commercial variety 'PHALIFSIB' in that 'PHALGRYCHI' has triangular apical lobes and whiskers that are white with few flecks of RHS N79C and light greenish-yellow tips, whereas 'PHALIFSIB' has trullate apical lobes and whiskers that are white with yellow tips. Additionally, 'PHALGRYCHI' has longer whiskers and smaller flowers than 'PHALIFSIB'.

I claim:

1. A new and distinct variety of *Phalaenopsis* plant named 'PHALGRYCHI', substantially as described and illustrated herein.

* * * * *